(12) United States Patent
Helenbolt et al.

(10) Patent No.: US 9,861,417 B2
(45) Date of Patent: Jan. 9, 2018

(54) OSTEOTOMY OPENING JACK

(71) Applicant: ARTHREX, INC., Naples, FL (US)

(72) Inventors: Kenneth T. Helenbolt, Naples, FL (US); Anthony A. Laviano, Fort Myers, FL (US); Michael E. Eggert, Lake Elmo, MN (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 15/220,899

(22) Filed: Jul. 27, 2016

(65) Prior Publication Data

US 2016/0331430 A1    Nov. 17, 2016

Related U.S. Application Data

(63) Continuation of application No. 14/206,912, filed on Mar. 12, 2014, now Pat. No. 9,414,877.

(60) Provisional application No. 61/779,616, filed on Mar. 13, 2013.

(51) Int. Cl.
| | |
|---|---|
| *A61B 17/88* | (2006.01) |
| *A61B 17/02* | (2006.01) |
| *A61B 17/15* | (2006.01) |
| *A61B 17/56* | (2006.01) |
| *A61B 17/68* | (2006.01) |

(52) U.S. Cl.
CPC ...... *A61B 17/8858* (2013.01); *A61B 17/8852* (2013.01); *A61B 17/8866* (2013.01); *A61B 17/025* (2013.01); *A61B 17/152* (2013.01); *A61B 2017/565* (2013.01); *A61B 2017/681* (2013.01)

(58) Field of Classification Search
CPC . A61B 17/025; A61B 17/152; A61B 17/8866; A61B 17/8852; A61B 17/885
See application file for complete search history.

(56) References Cited

U.S. PATENT DOCUMENTS

| | | |
|---|---|---|
| 2005/0251147 A1 | 11/2005 | Novak |
| 2008/0262500 A1 | 10/2008 | Collazo |

FOREIGN PATENT DOCUMENTS

| | | |
|---|---|---|
| EP | 2036509 A1 | 3/2009 |

OTHER PUBLICATIONS

"The iBalance HTO Opening Jack," Arthrex, Inc., 2010.

*Primary Examiner* — Andrew Yang
(74) *Attorney, Agent, or Firm* — Carlson, Gaskey & Olds

(57) ABSTRACT

Adjustable opening jacks with designs that incorporate a novel locking hinge mechanism and adjustable separation arms to achieve broader scopes of application, bone plate specificity, and variable bone size capability during various osteotomy procedures. The locking hinge mechanism constrains the upper body from moving in either the vertical plane or anterior-posterior (AP) slope trajectory depending on the mode of application. The opening jack has a configuration that allows for a straight and/or sloped opening.

14 Claims, 22 Drawing Sheets

OSTEOTOMY OPENING JACK

CROSS-REFERENCE TO RELATED APPLICATIONS

This application is a continuation of U.S. patent application Ser. No. 14/206,912, filed Mar. 12, 2014, which claims the benefit of U.S. Provisional Application No. 61/779,616, filed Mar. 13, 2013. The disclosures of these prior applications are incorporated by reference in their entirety herein.

FIELD OF THE INVENTION

The present invention relates to the field of surgery and, more particularly, to instruments and methods for osteotomies.

BACKGROUND OF THE INVENTION

Knee osteotomies are used to relieve pain symptoms, slow disease progression and postpone total knee arthroplasty. For example, to treat lower extremity malalignment and osteoarthritis, a high tibial osteotomy is employed to allow for the realignment of the lower extremity and, thus, either shift the weight-bearing access to the healthier portion of the knee or correct the alignment deformity. This procedure is performed by cutting the tibia and, with the use of an opening jack, allows the surgeon to dial in the exact correction desired to correct the angular deformity or shift the weight-bearing axis to a desired position in the knee. An anatomically precontoured low profile plate and screws are applied or a nonabsorbable PEEK implant and anchors are inserted to maintain and fixate the osteotomy.

There is a need for an opening jack that can provide a sloped or non-sloped opening depending on the surgeon's preference and on the plate used. Also needed are osteotomy procedures that prevent stress and macro fractures of the lateral bone cortex.

SUMMARY OF THE INVENTION

The present invention provides adjustable opening jacks with designs that incorporate a novel locking hinge mechanism and adjustable separation arms to achieve broader scopes of application, bone plate specificity, and variable bone size capability during various osteotomy procedures. The locking hinge mechanism constrains the upper body from moving in either the vertical plane or anterior-posterior (AP) slope trajectory depending on the mode of application. The opening jack has a configuration that allows for a straight and/or sloped opening.

These and other features and advantages will become apparent from the following description that is provided in connection with the accompanying drawings and illustrated embodiments.

DETAILED DESCRIPTION OF THE PREFERRED EMBODIMENTS

Figure 1:
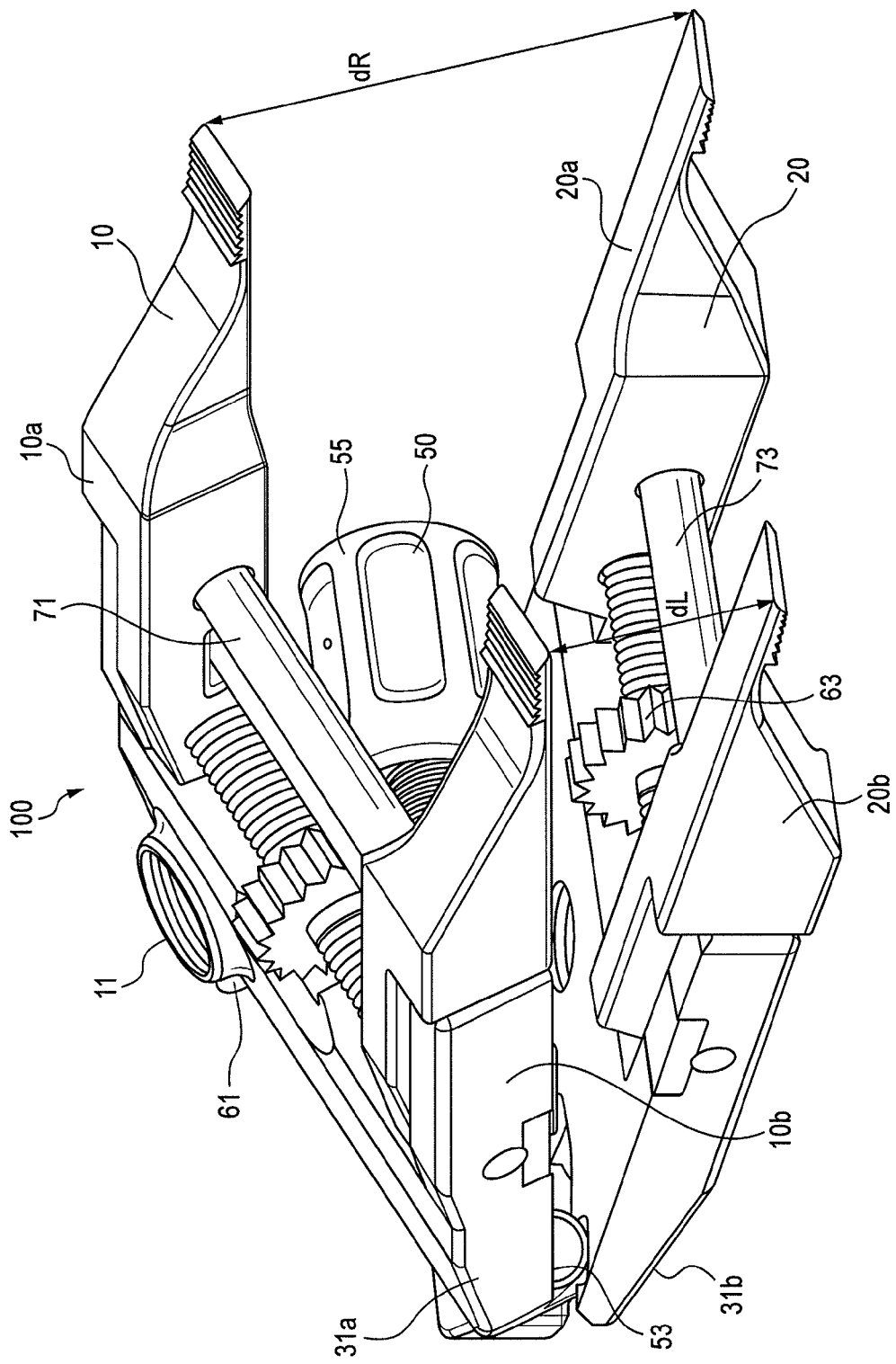
FIG. 1 illustrates an exemplary opening jack assembly that uses a hinge lock, adjustable arm mechanism, and double sided adjustment screw holes according to a first embodiment of the present invention (opening AP slope, isometric view).

The present invention provides osteotomy methods and adjustable osteotomy opening jacks that incorporate novel hinge mechanisms and adjustable separation arms to achieve broader scopes of application, bone plate specificity, and variable bone size capability during various osteotomy procedures. The locking hinge mechanisms constrain the upper body from moving in either the vertical plane or anterior-posterior (AP) slope trajectory depending on mode of application. The opening jack may be provided as part of an osteotomy system that includes positioning guides, cutting guides and corresponding cutting instruments, as well as implants for supporting the open wedge osteotomy in tibia and accompanying osteotomy plates.

The adjustable osteotomy jack of the present invention comprises a pair of adjustable plates or bodies (a first plate and a second plate) connected by a hinge lock mechanism that allows the first plate and the second plate of the opening jack to open in a straight or sloped configuration. The hinge lock mechanism includes a locking knob, a hinge shaft, a shaft link and an angle hinge shaft, the hinge shaft being attached to the locking knob at one end and to the shaft link at the other end. Each of the first and second plates is formed of a right arm and a left arm. The right and left arms of each of the first and second plates are about similar. Actuation of the hinge lock mechanism causes the arms to move relative to each other and to various openings and dimensions, as explained in more detail below.

Each of the first and second plates is also provided with a first end and a second end in opposition to one another, the first end of the pair of plates being configured to remain substantially together with one another, and the second end of the pair of plates being configured for placement into the bone cut in the tibia and for selective positioning by actuating the hinge lock mechanism from (a) a first position with the second end of the pair of plates substantially together with one another to (b) a second position with the second end of the pair of plates apart from one another and with the distance between the right arm of the first plate and the right arm of the second plate being about equal to the distance between the left arm of the first plate and the left arm of the second plate, and/or to (c) a third position with the second end of the pair of plates apart from one another and with the distance between the right arm of the first plate and the right arm of the second plate being different from the distance between the left arm of the first plate and the left arm of the second plate.

The present invention also provides a method for performing an opening wedge osteotomy in a bone, the method comprising inter alia the steps of: (i) forming a cut in bone; (ii) providing a mechanical jack comprising a pair of adjustable bodies or plates, the pair of plates having a first end and a second end in opposition to one another, the first end of the pair of plates being configured to remain substantially together with one another, and the second end of the pair of plates being configured for placement into the bone cut and for selective positioning from (a) a first position wherein the second end of the pair of plates are substantially together with one another to (b) a second position wherein the second end of the pair of plates are apart from one another and in symmetry with one another, and/or to (c) a third position wherein the second end of the pair of plates are apart from one another and in non-symmetry with one another; (iii) positioning the second ends of the pair of plates of the mechanical jack into the tibia cut, the pair of plates having their second ends in the first position wherein the second ends of the pair of plates are substantially together; and (iv) actuating the mechanical jack to move the second ends of the pair of plates from the first position to the second position or the third position wherein the second ends of the pair of plates are apart from each other and either in symmetry or non-symmetry, to distract the bone at the bone cut.

An exemplary method for performing an opening wedge, high tibial osteotomy comprises inter alia the steps of: (i) forming an osteotomy cut in tibia; (ii) providing a mechanical jack comprising a pair of adjustable bodies or plates and a locking hinge mechanism attached to the pair of adjustable bodies or plates, the locking hinge mechanism comprising a locking knob, a horizontal hinge shaft, a shaft link and an angle hinge shaft, each of the first and second plates being formed of a right arm and a left arm, the pair of plates having a first end and a second end in opposition to one another, the first end of the pair of plates being configured to remain substantially together with one another, and the second end of the pair of plates being configured for placement into the bone cut in the tibia and for selective positioning from (a) a first position wherein the second end of the pair of plates are substantially together with one another to (b) a second position wherein the second end of the pair of plates are apart from one another and with the distance between the right arm of the first plate and the right arm of the second plate being about equal to the distance between the left arm of the first plate and the left arm of the second plate, and/or to (c) a third position wherein the second end of the pair of plates are apart from one another and with the distance between the right arm of the first plate and the right arm of the second plate being different from the distance between the left arm of the first plate and the left arm of the second plate; (iii) positioning the second ends of the pair of plates of the mechanical jack into the tibia cut, the pair of plates having their second ends in the first position wherein the second ends of the pair of plates are substantially together; (iv) actuating the mechanical jack to move the second ends of the pair of plates from the first position to the second position or the third position wherein the second ends of the pair of plates are apart from each other, to distract the tibia at the osteotomy cut and to form a wedge-like opening; and (v) providing an osteotomy plate and securing the osteotomy plate against the tibia and at the wedge-like opening.

Figure 20:
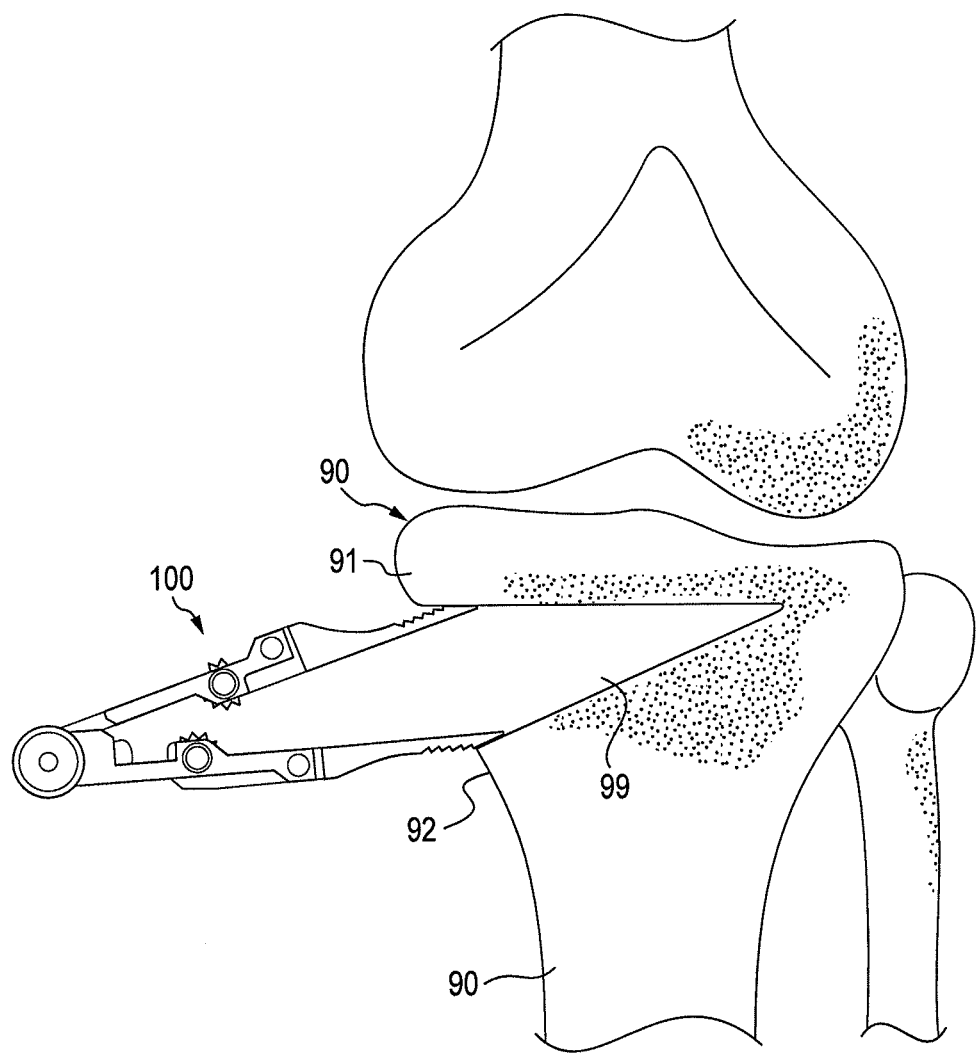
FIG. 20 illustrates the opening jack assembly of FIG. 1 employed in an open wedge osteotomy in a tibia.

Referring now to the drawings, where like elements are designated by like reference numerals, FIGS. 1-19 illustrate opening jack assemblies 100, 200, 300 (opening jacks 100, 200, 300) according to various exemplary embodiments of the present invention. FIG. 20 illustrates exemplary opening jack 100 of the present invention as part of an open wedge osteotomy technique in a tibia. The opening jack 100, 200, 300 is provided with a configuration that allows for a straight and/or sloped opening (i.e., uniform and/or non-uniform opening). A single opening jack 100, 200, 300 can provide either a sloped or nonsloped opening depending on the surgeon's preference and the plate used. The opening jack 100, 200, 300 is a mechanical osteotomy opening jack that has an adjustable opening jack design.

FIGS. 1-13 illustrate a first exemplary embodiment of opening jack 100 of the present invention that uses a hinge lock, adjustable arm mechanism, and double-sided adjustment screw holes. As detailed below, the adjustable opening jack 100 incorporates a novel locking hinge mechanism 50 and adjustable separation arms 10, 20 to achieve broader scopes of application, bone plate specificity, and variable bone size capability during various osteotomy procedures. The locking hinge mechanism 50 provides a non-uniform opening, i.e., constrains the upper body from moving in either the vertical plane or anterior-posterior (AP) slope trajectory depending on the mode of application.

The adjustable opening jack design incorporates a novel locking hinge mechanism and adjustable separation arms to achieve broader scopes of application, bone plate specificity, and variable bone size capability during various osteotomy procedures. The locking hinge mechanism constrains the upper body from moving in either the vertical plane or anterior-posterior (AP) slope trajectory depending on mode of application.

Figure 1A:
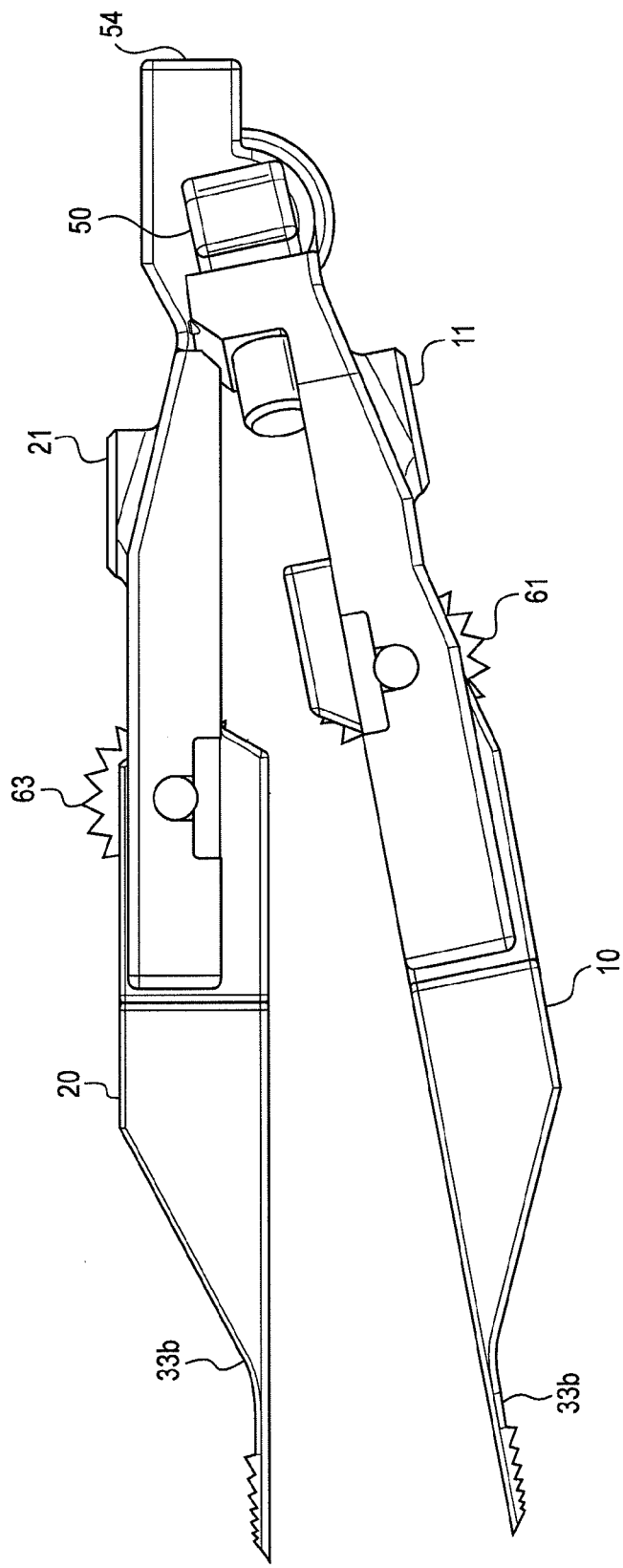
FIG. 1A illustrates a side view of the opening jack assembly of FIG. 1 (vertical opening, side view).

FIGS. 1 and 1(*a*) illustrate opening jack assembly 100 with a pair of adjustable plates 10, 20 (also referred to as first and second plates, or first and second bodies, or upper and lower plates) that use hinge lock 50 (locking hinge mechanism 50) for an opening AP slope (FIG. 1) and/or a vertical opening (FIG. 1*a*).

Each of the pair of adjustable plates 10, 20 is provided with a first (right) and second (left) arm 10*a*, 10*b* and 20*a*, 20*b*, respectively. Upper plate 10 is provided with a right upper arm 10*a* (first upper arm 10*a*) and a left upper arm 10*b* (second upper arm 10*b*), as shown in FIG. 1. Lower plate 20 is provided with a right lower arm 20*a* (first lower arm 20*a*) and a left lower arm 20*b* (second lower arm 20*b*), as also shown in FIG. 1.

Each of the pair of adjustable plates of the mechanical osteotomy jack is also provided with a first end 31*a*, 31*b* and a second end 33*a*, 33*b* in opposition to one another, the first end 31*a*, 31*b* of the pair of plates being configured to remain substantially together with one another, and the second end 33a, 33b of the pair of plates being configured for placement into the bone cut in the tibia and for selective positioning from (i) a first position with the second end 33a, 33b of the pair of plates 10, 20 substantially together with one another to (ii) a second position with the second end of the pair of plates apart from one another and with the distance "dR" between the right arm of the first plate and the right arm of the second plate being about equal to the distance "dL" between the left arm of the first plate and the left arm of the second plate, and/or to (iii) a third position with the second end of the pair of plates apart from one another and with the distance dR between the right arm of the first plate and the right arm of the second plate being different from the distance dL between the left arm of the first plate and the left arm of the second plate. Distances dR and dL are calculated, for simplicity, from a most distal end of each of the arms 10a, 10b, 20a, 20b.

In the second and third positions, the opening formed by the spaced apart pair of plates may have a sloped or non-sloped configuration.

Figure 7:
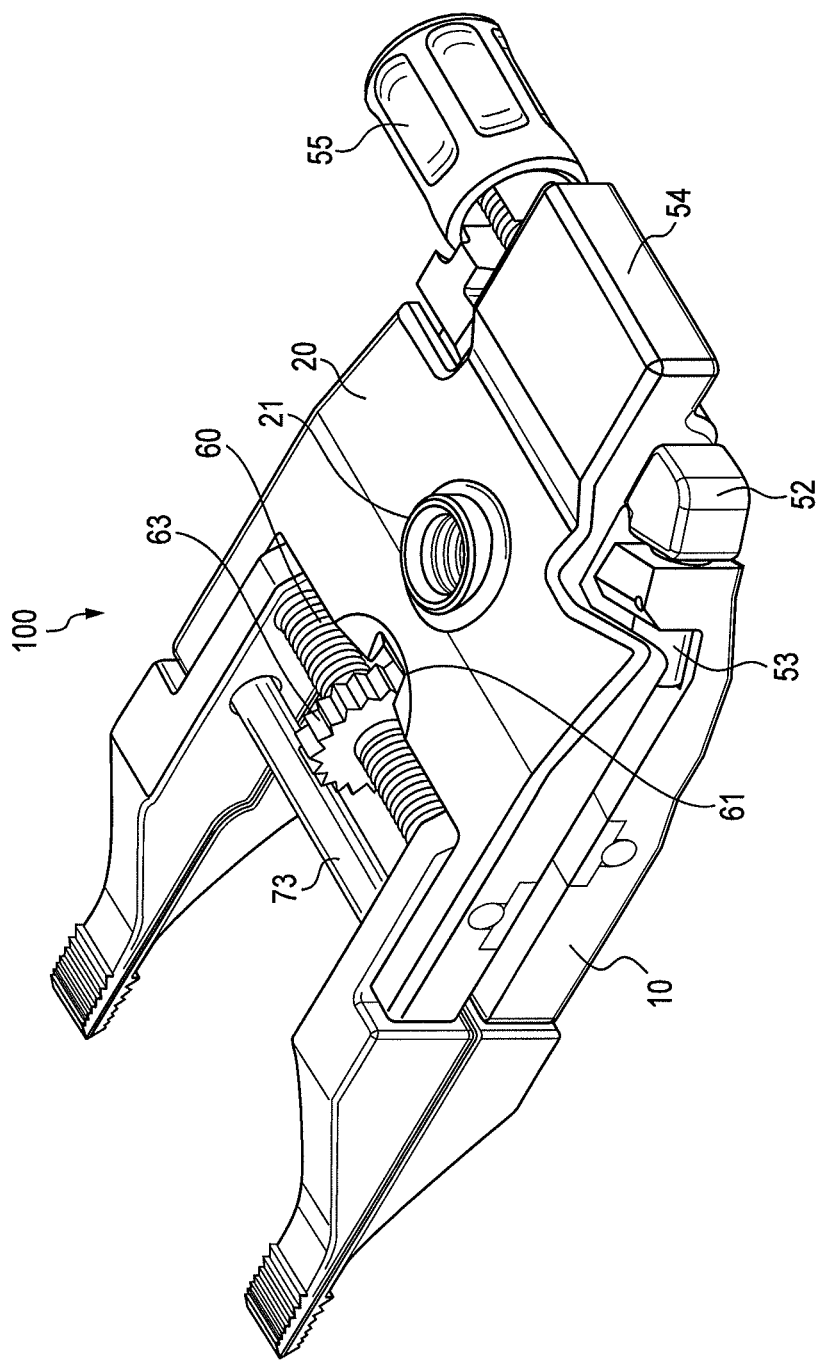
FIG. 7 illustrates a perspective bottom view of the opening jack assembly of FIG. 1.
Figure 8:
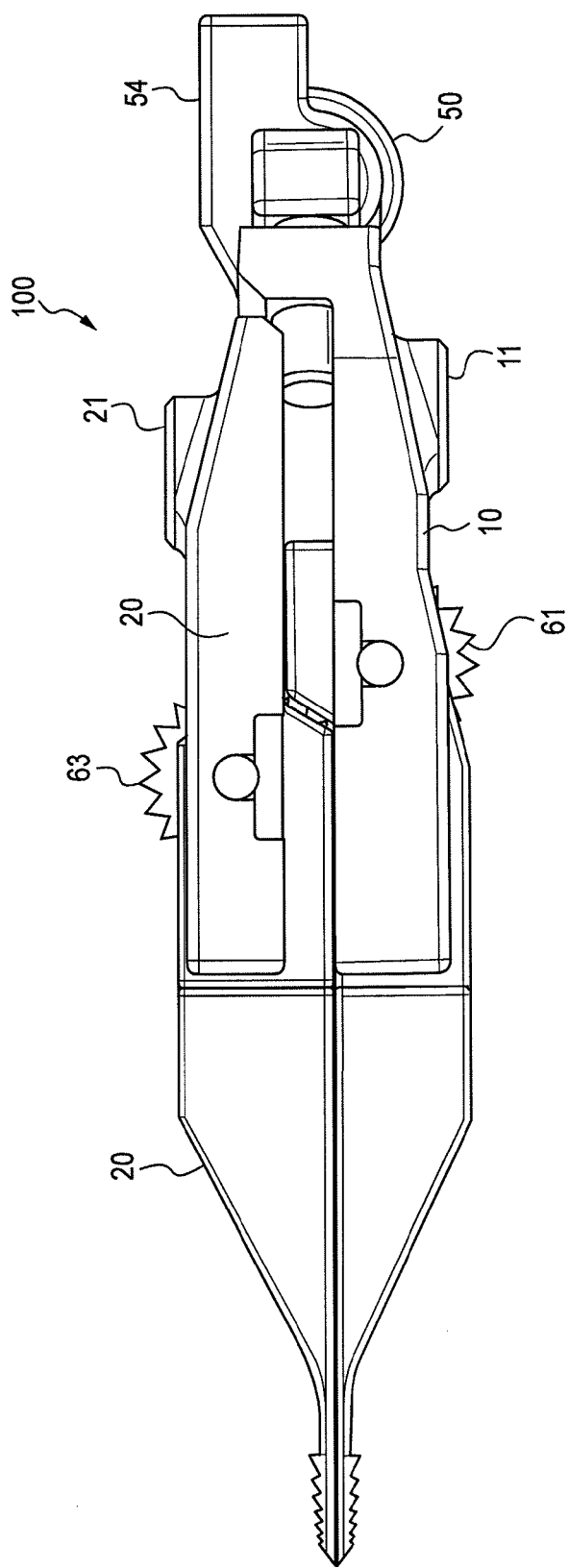
FIG. 8 illustrates a left side view of the assembly of FIG. 7.
Figure 9:
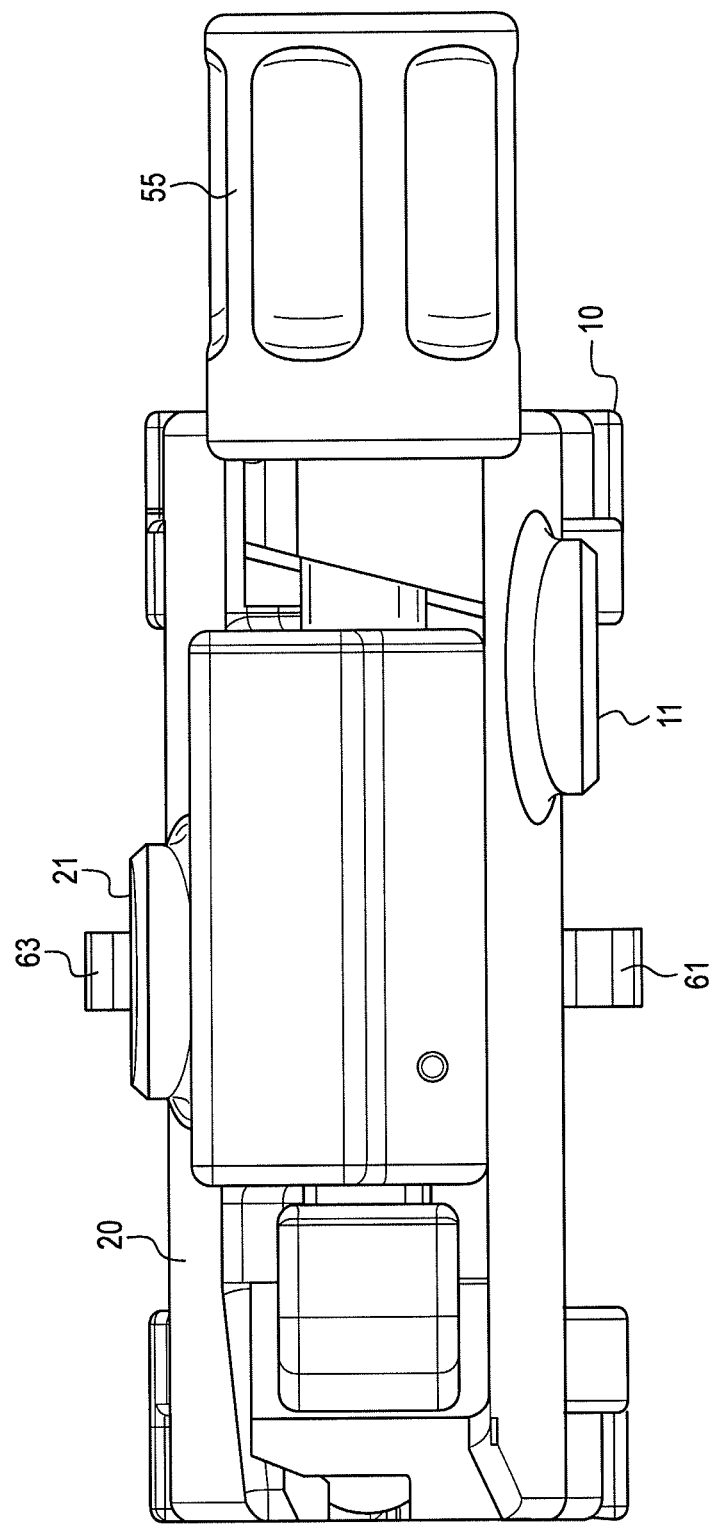
FIG. 9 illustrates a back view of the assembly of FIG. 7.
Figure 10:
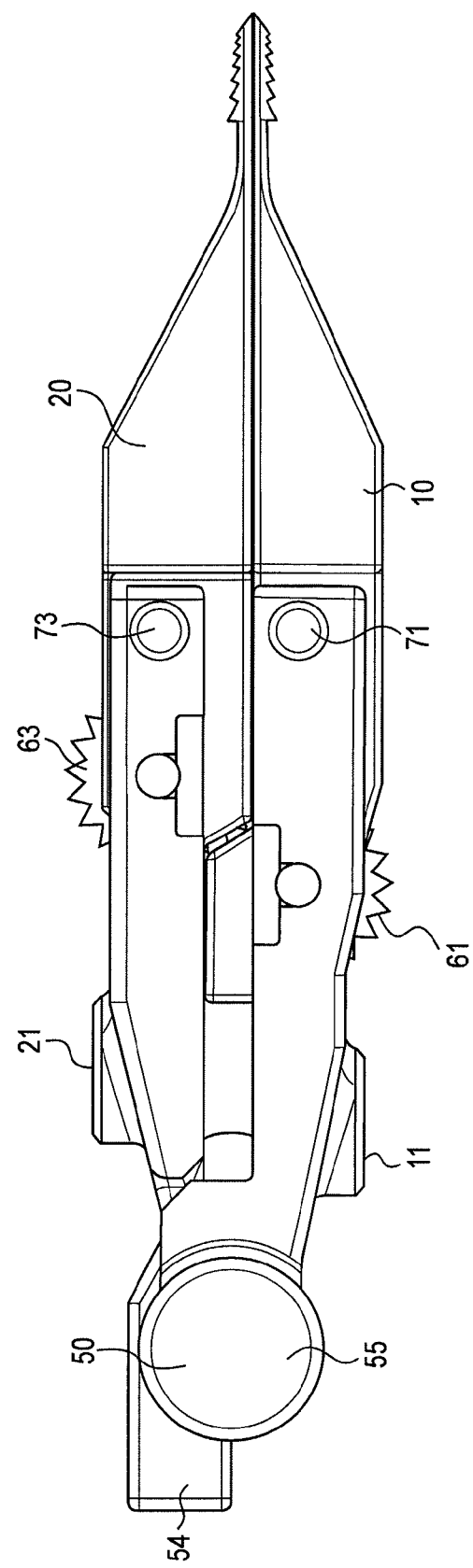
FIG. 10 illustrates a right side view of the assembly of FIG. 7.
Figure 11:
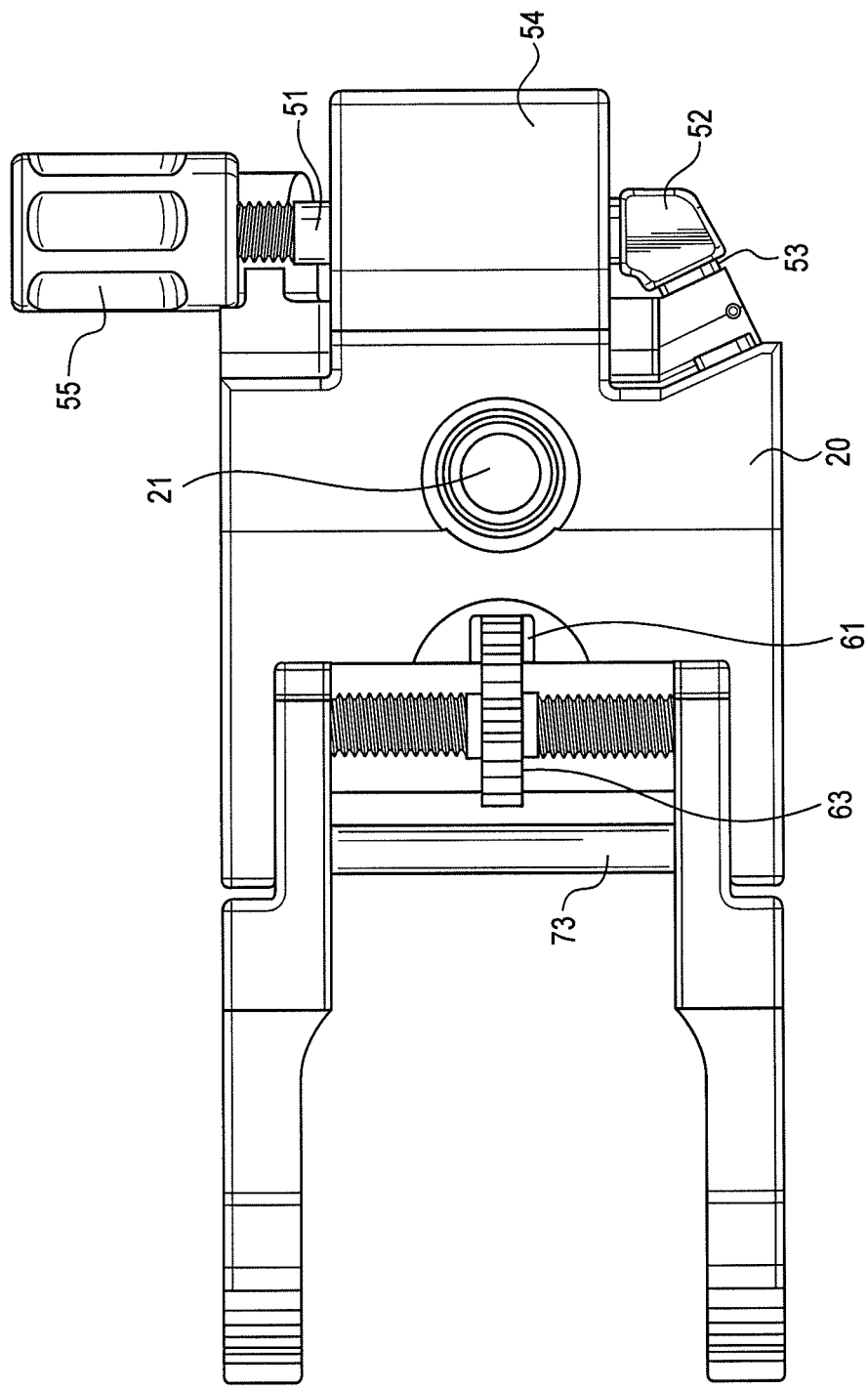
FIG. 11 illustrates a top view of the assembly of FIG. 7.
Figure 12:
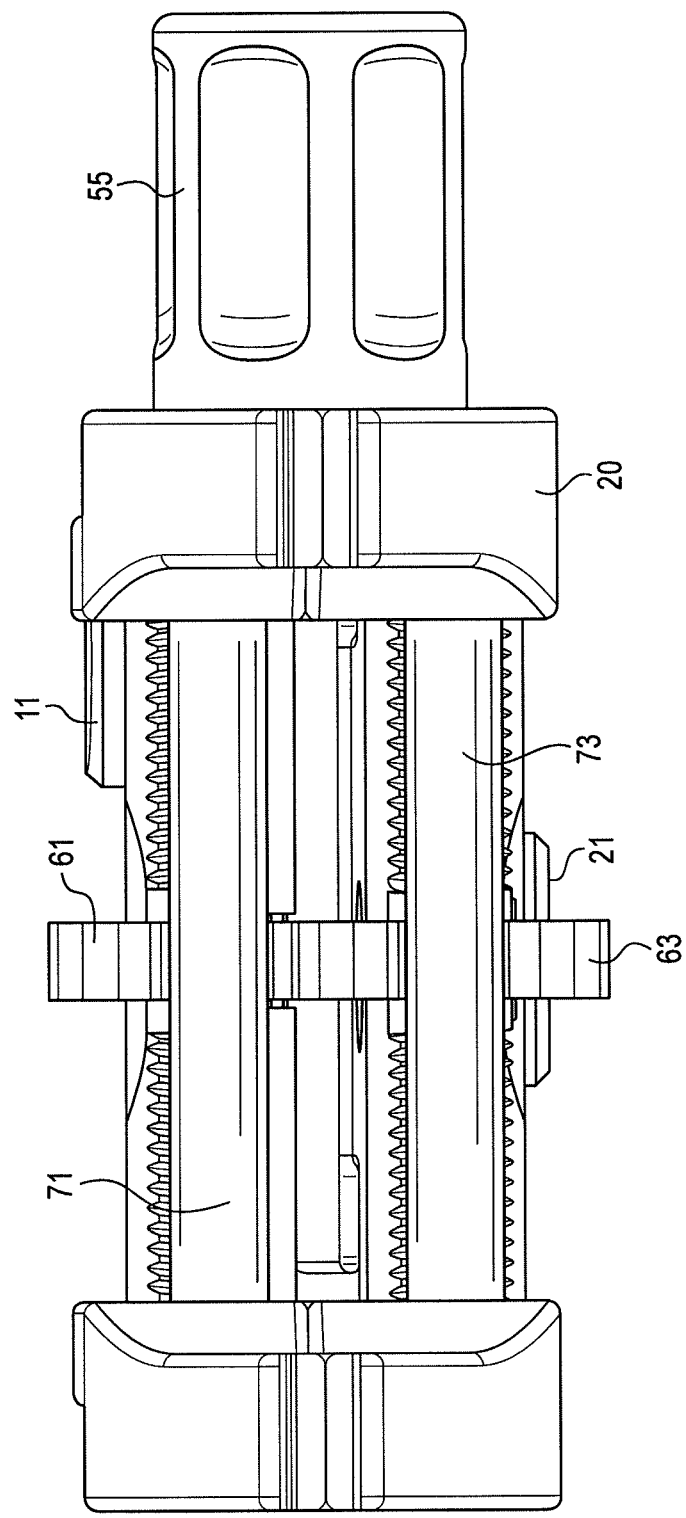
FIG. 12 illustrates a front view of the opening jack assembly of FIG. 7.
Figure 13:
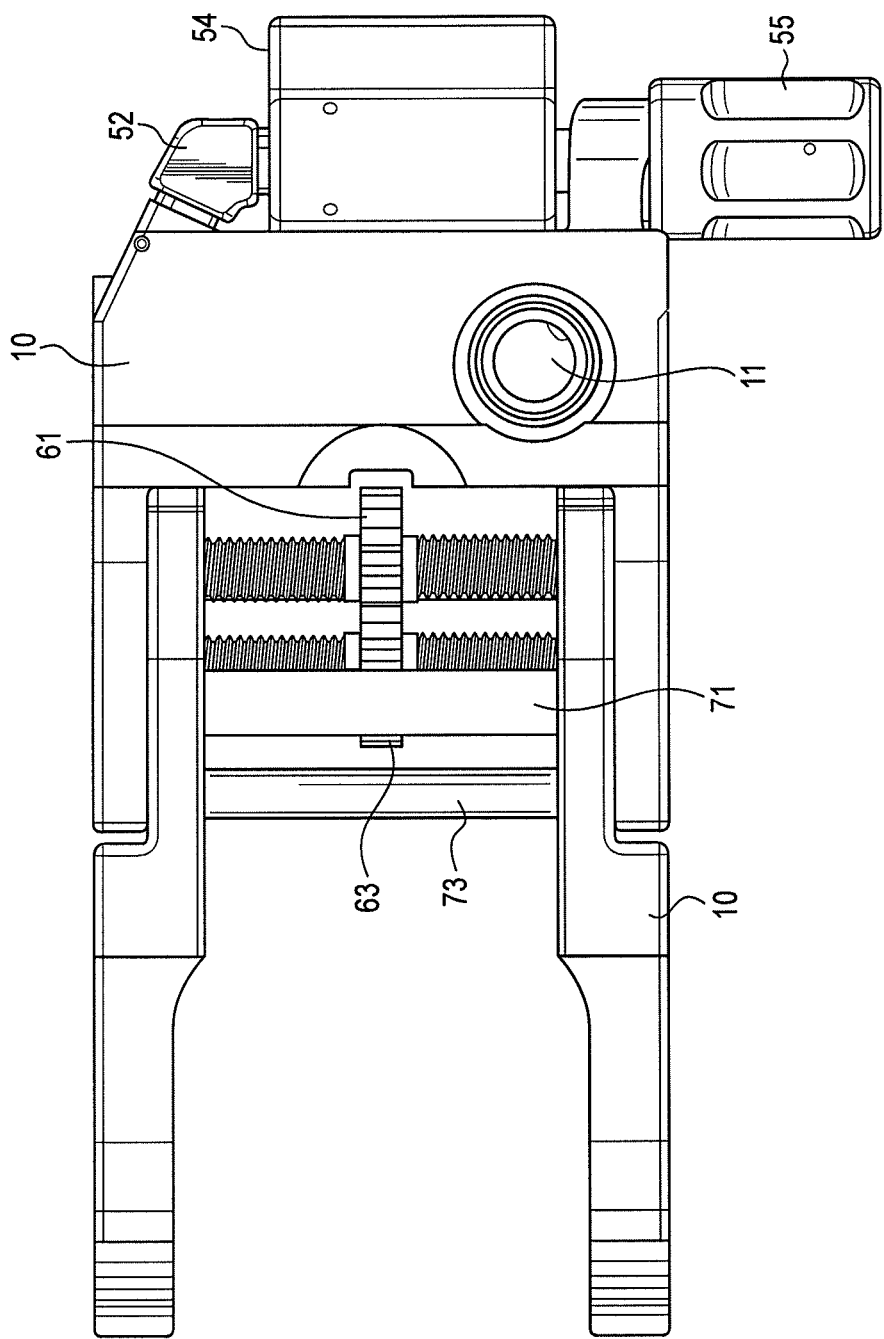
FIG. 13 illustrates a bottom view of the assembly of FIG. 7.

The first position wherein the second end 33a, 33b of the pair of plates 10, 20 is substantially together with one another is shown, for example, in FIG. 7. The second position is shown in FIG. 1(a) and the third position is shown in FIG. 1.

FIG. 1 also illustrates adjustable gear 61 (upper arm adjustable gear 61 or upper adjustable gear 61) with corresponding reverse thread adjustable bolt 62 (provided with a lateral pin 62a), and adjustable gear 63 (lower arm adjustable gear 63 or lower adjustable gear 63) with corresponding reverse thread adjustable bolt 64 (provided with a lateral pin 64a), as well as guide posts 71, 73 (upper guide post 71 and lower guide post 73). Details of adjustable gears 61, 63, of corresponding reverse thread adjustable bolts 62, 64 and guide posts 71, 73 are shown for example in FIG. 5(a).

Figure 2:
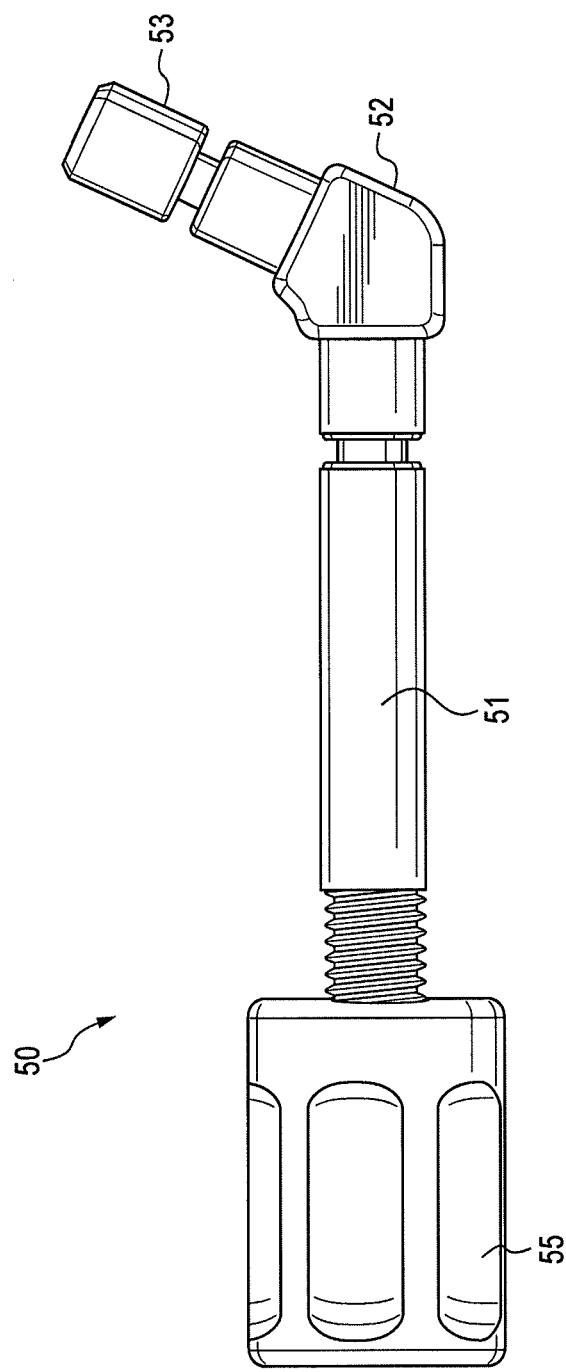
FIG. 2 illustrates the hinge shaft weldment of the opening jack of FIG. 1.

FIG. 2 illustrates an enlarged view of the locking hinge mechanism 50 (with hinge shaft weldment) of the opening jack 100. As shown in FIG. 2, the main components of the hinge mechanism 50 include a horizontal hinge shaft 51 that interfaces with a locking knob 55 (lock knob 55), a shaft link 52 and an angle hinge shaft 53. The three component hinge shaft weldment allows and prevents user selected opening configurations (either vertical or AP opening).

Figure 3:
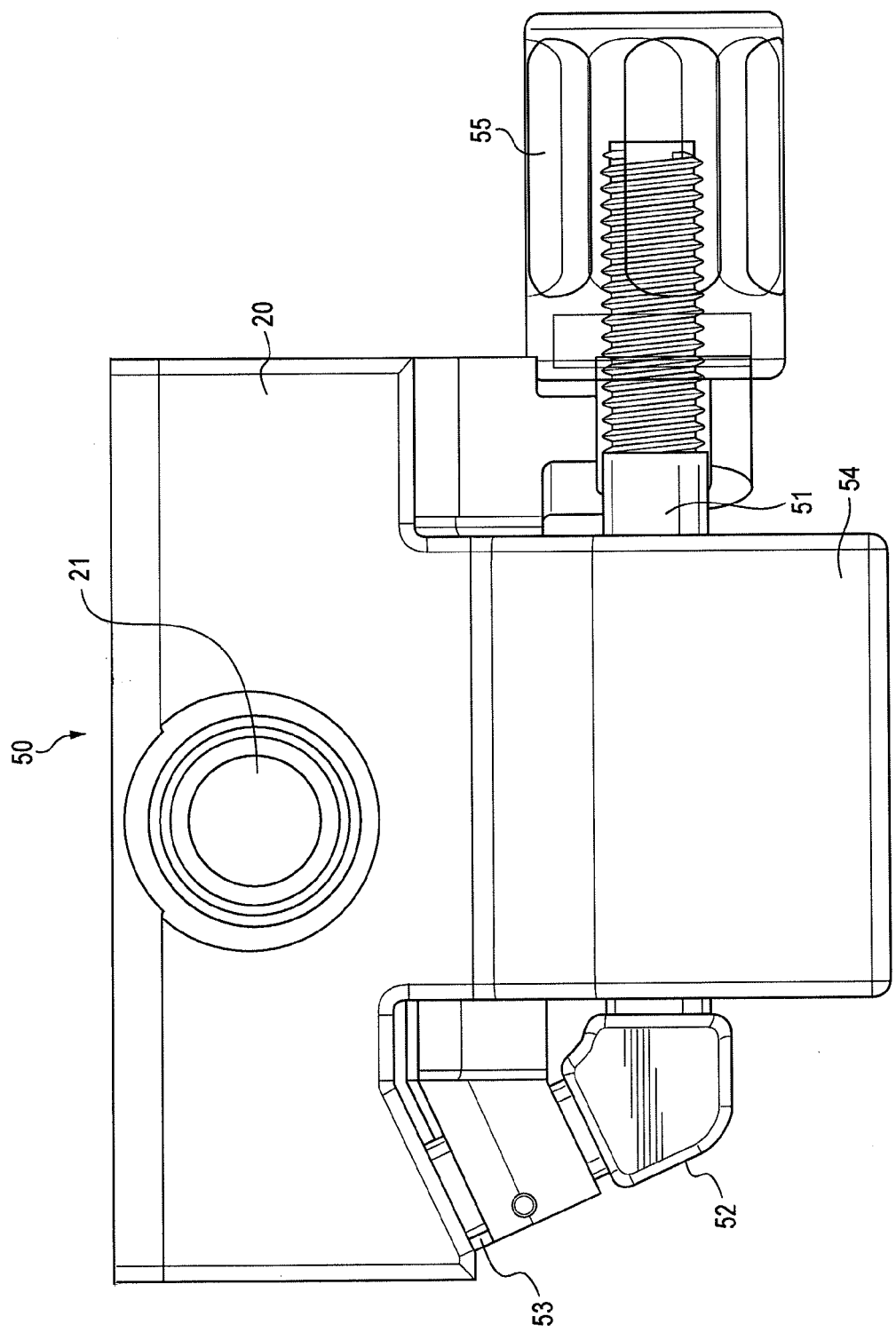
FIG. 3 illustrates the assembled hinge lock mechanism (with the upper body rendered transparent) of the opening jack of FIG. 1.

FIG. 3 illustrates the assembled hinge lock mechanism 50, i.e., the working assembly of the locking hinge shaft with the upper body and locking knob shown as transparent for visual clarity of the hinge locking mechanism. FIG. 3 also shows plate 54 (insertion impact plate 54) as part of one of the arms 10, 20, for example, as part of the lower arm 20 (second arm 20) of the opening jack 100.

Figure 4:
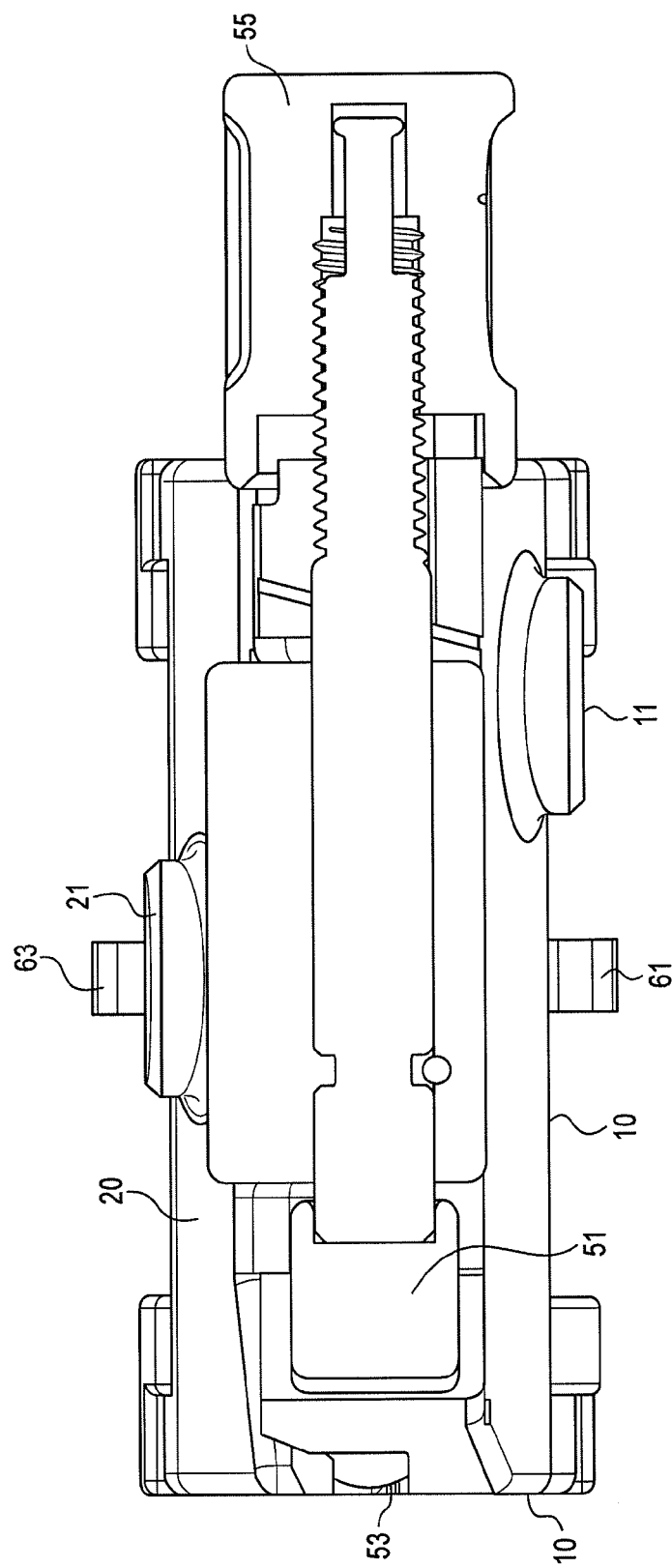
FIG. 4 illustrates a posterior sectional view of the hinge locking mechanism of the opening jack of FIG. 1.

FIG. 4 illustrates a posterior sectional view of the hinge locking mechanism 50 of the present invention, illustrating the interface between the horizontal hinge shaft 51 and locking knob 55. The locking knob 55 (lock knob 55) and hinge shaft 51 are threaded, and the knob 55 is captured (by pin) to prevent detachment from the main device. The locking knob 55 uses a smaller inner diameter to sit within the larger inner diameter bore of the interfacing part feature. This arrests the upper and lower bodies 10, 20 when screwed on tightly and only allows vertical opening, as shown in FIG. 1(a). Alternatively, when the locking knob 55 is completely loosened, rotation only occurs about the angled hinge shaft allowing for opening of AP slope, as illustrated in FIG. 1.

When the locking knob 55 is actuated (rotated) in a first direction (for example, a clockwise direction), the first and second plates 10, 20 are locked and a vertical opening is allowed between the first and second plates. When the locking knob is further actuated (rotated) in a second direction which is different from the first direction (for example, in a counterclockwise direction), the first and second plates are opening at various anterior-posterior (AP) angles.

The main components of the hinge 50 are the horizontal shaft 51 that interfaces with the locking knob 55, shaft link 52 and angled hinge shaft 53 (as also shown in FIGS. 2 and 3). The three-component hinge shaft weldment allows and prevents user selected opening configurations (either vertical or AP opening, as seen in FIG. 1).

Figure 5:
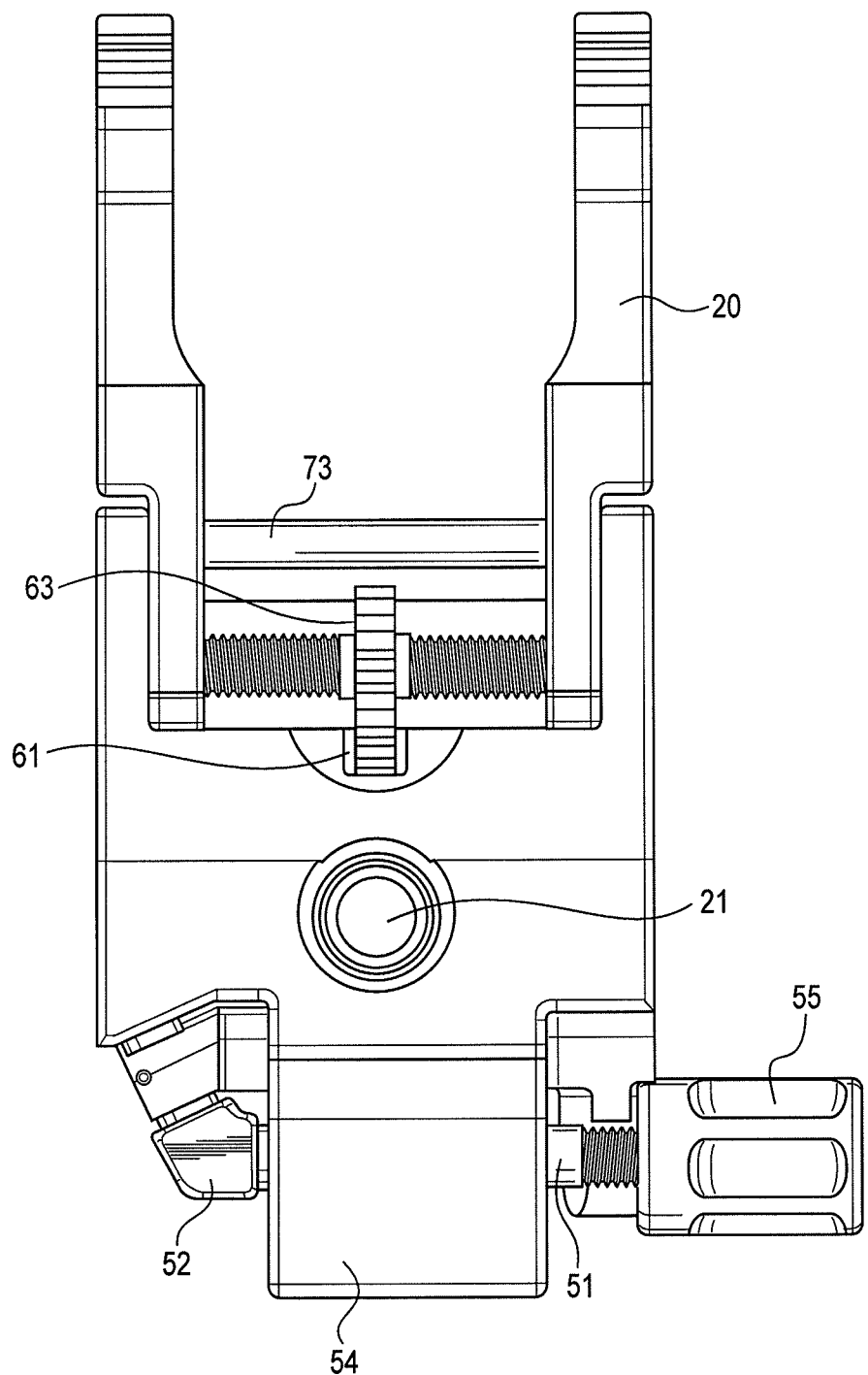
FIG. 5 illustrates a bottom view of the opening jack assembly of FIG. 1 (adjustable opening jack design).
Figure 5A:
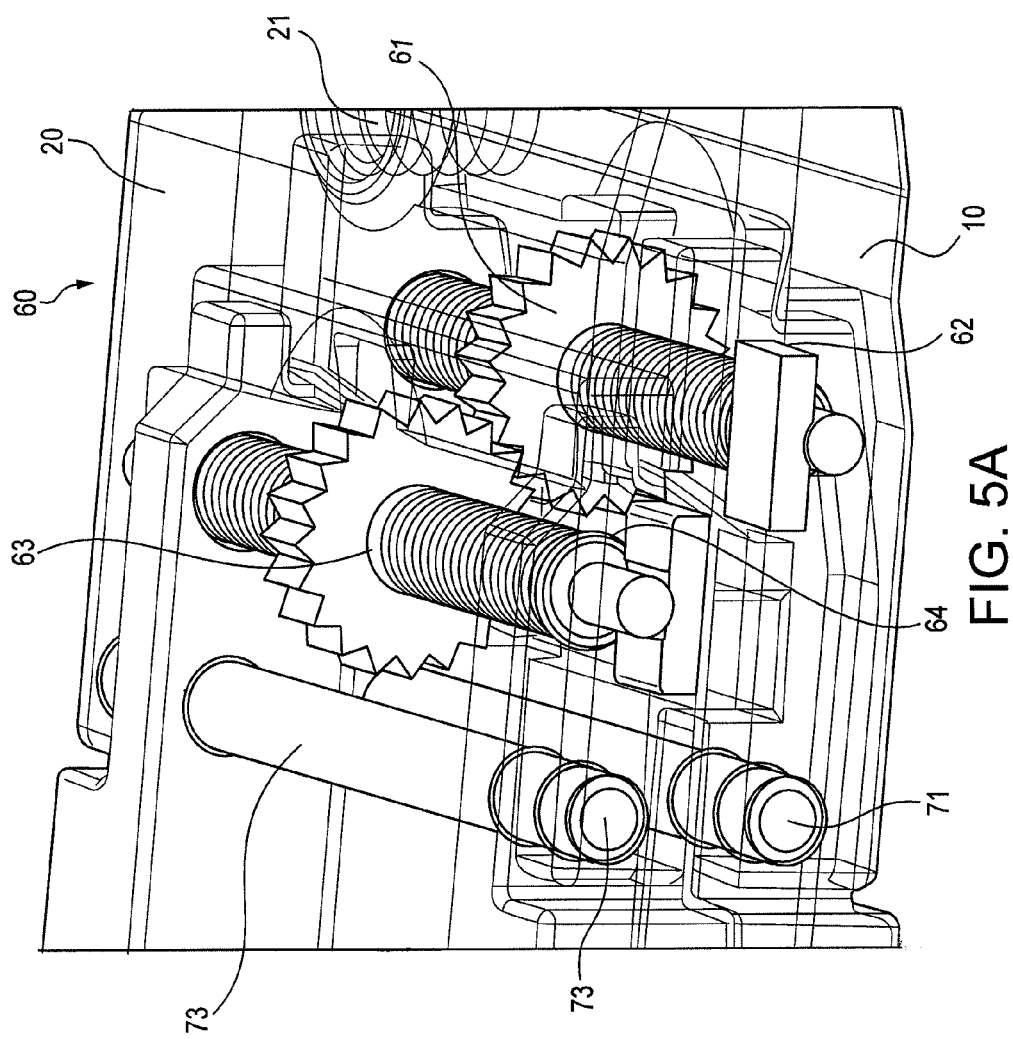
FIG. 5A illustrates a transparent internal view of adjustable arms for visual clarity of gear mechanism of the assembly of FIG. 5.

FIGS. 5 and 5(a) show the arm adjustment gear mechanism 60, which translates the upper and lower compression arms 10, 20 to increase or decrease separation. The upper and lower arms 10, 20 translate together when the interfacing surfaces of the upper and lower bodies and gears 61, 63 are coincident and parallel. FIG. 5(a) demonstrates this configuration and shows the position of the gears 61, 63 in their proper orientation for adjustment. Separation of the interfacing surfaces by opening the jack 100 in either the vertical or AP slope configurations prevents gear interfacing and retains compression arm position for desired separation during use. The significance of this design is that it provides optimal function for broader scopes of application, bone plate specificity, and variable bone size capability.

Figure 6:
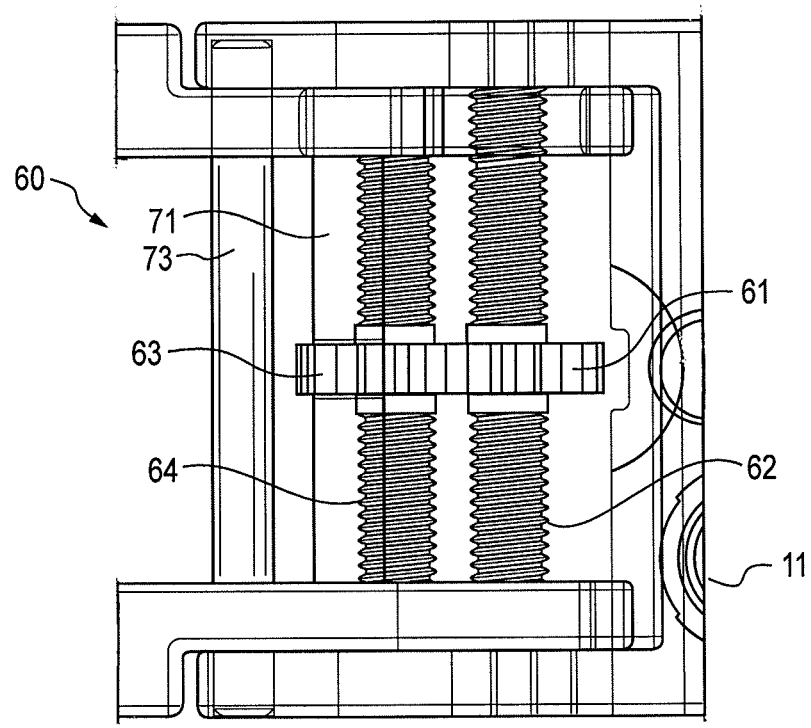
FIG. 6 illustrates a top view of the gear mechanism and threaded adjustment shafts of the opening jack of FIG. 1 (with a transparent view of adjustable arms for visual clarity).

FIG. 6 shows the gear mechanism 60 and threaded adjustment shafts 62, 64 (reverse thread adjustment bolts 62, 64) of the opening jack 100 (with a transparent view of adjustable arms 10, 20 for visual clarity). FIGS. 7-13 illustrate additional views of the opening jack assembly 100.

Other prototyped design concepts according to the present invention include as follows:
1. Adjustable hinge to achieve various AP slope angles;
11. Insertion impact plate; and/or
111. Gear locks to prevent involuntary separation of compression arms.

Figure 14:
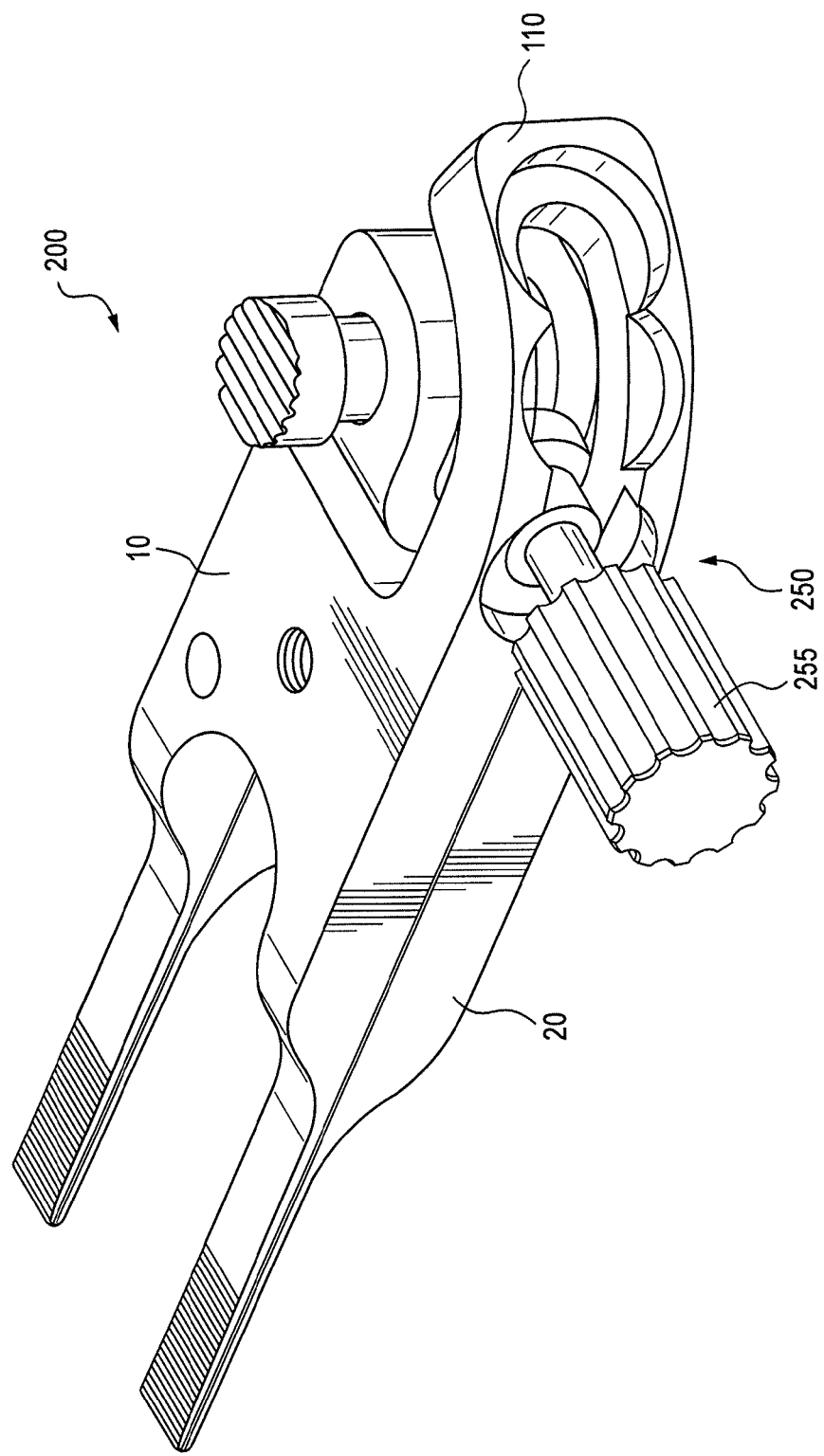
FIG. 14 illustrates a perspective view of an opening jack assembly according to a second embodiment of the present invention (in a first or closed position).
Figure 15:
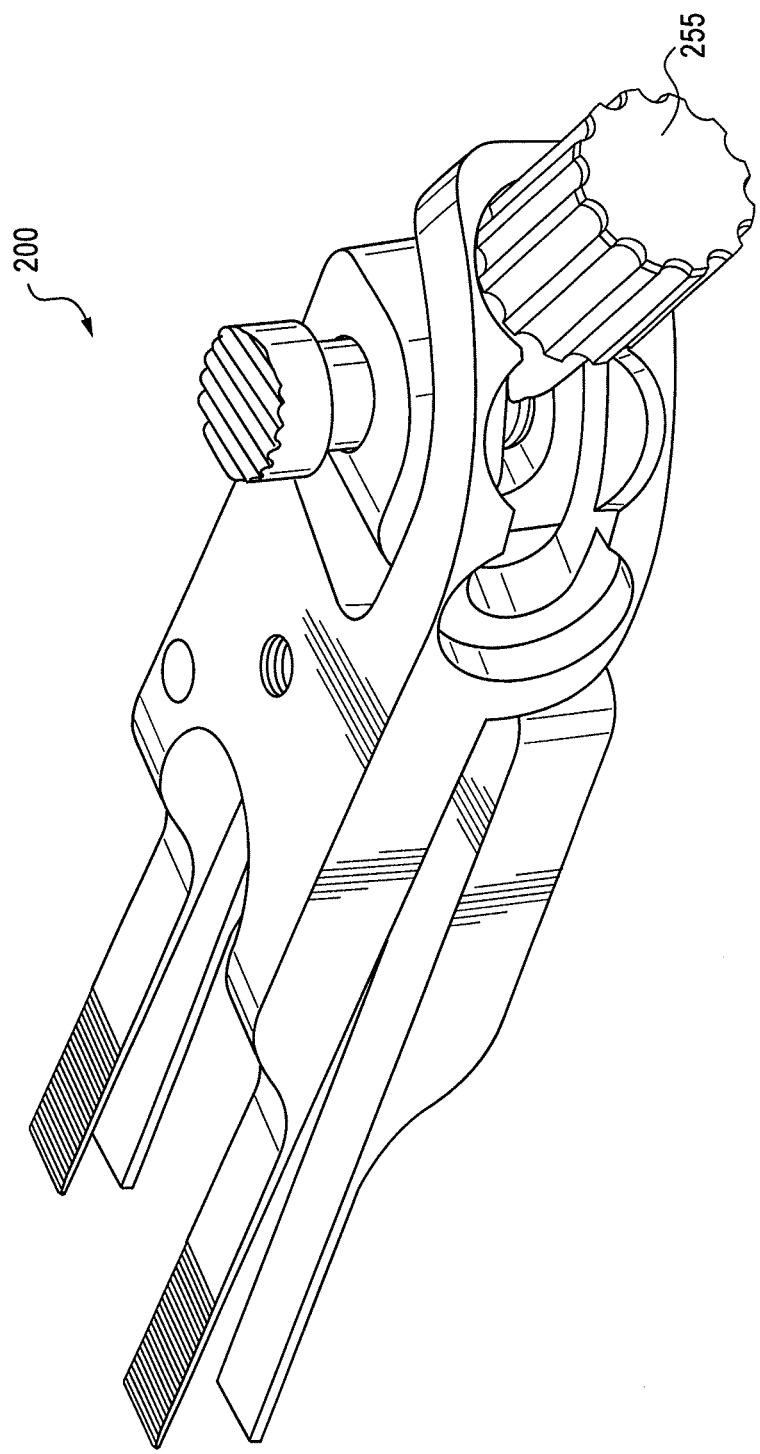
FIG. 15 illustrates another perspective view of the opening jack assembly of FIG. 14 (in a second or open position).
Figure 16:
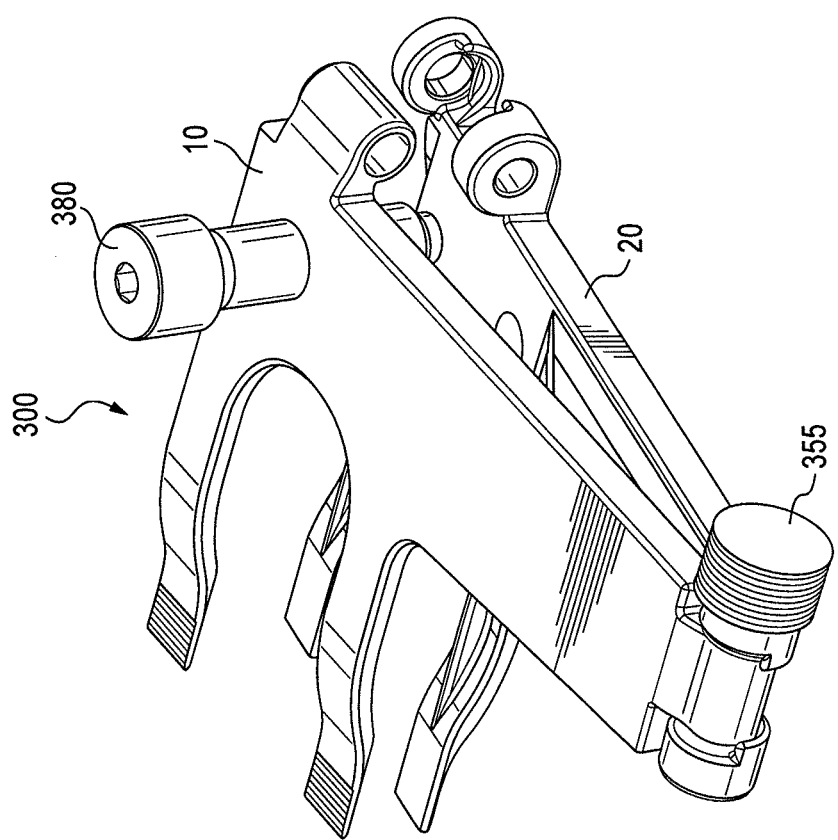
FIGS. 16-19 illustrate various views of an opening jack assembly according to a third embodiment of the present invention.
Figure 17:
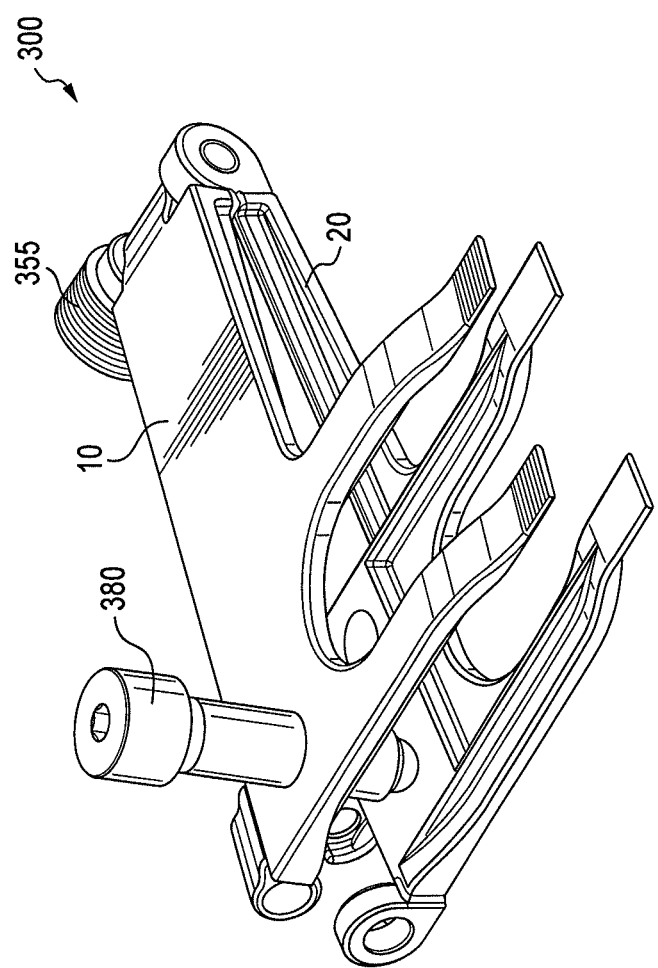
Figure 18:
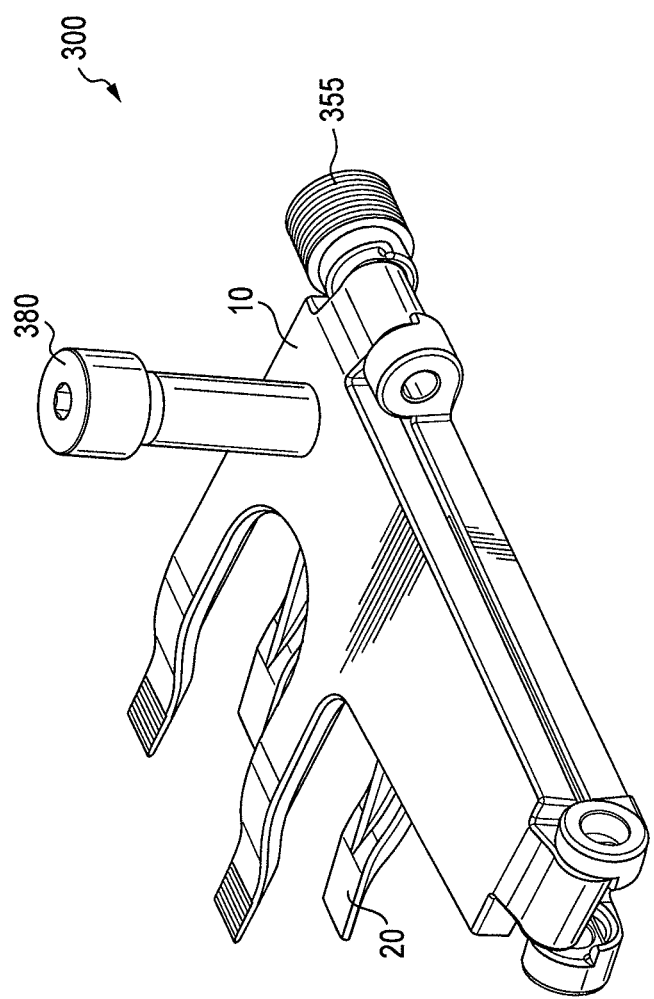
Figure 19:
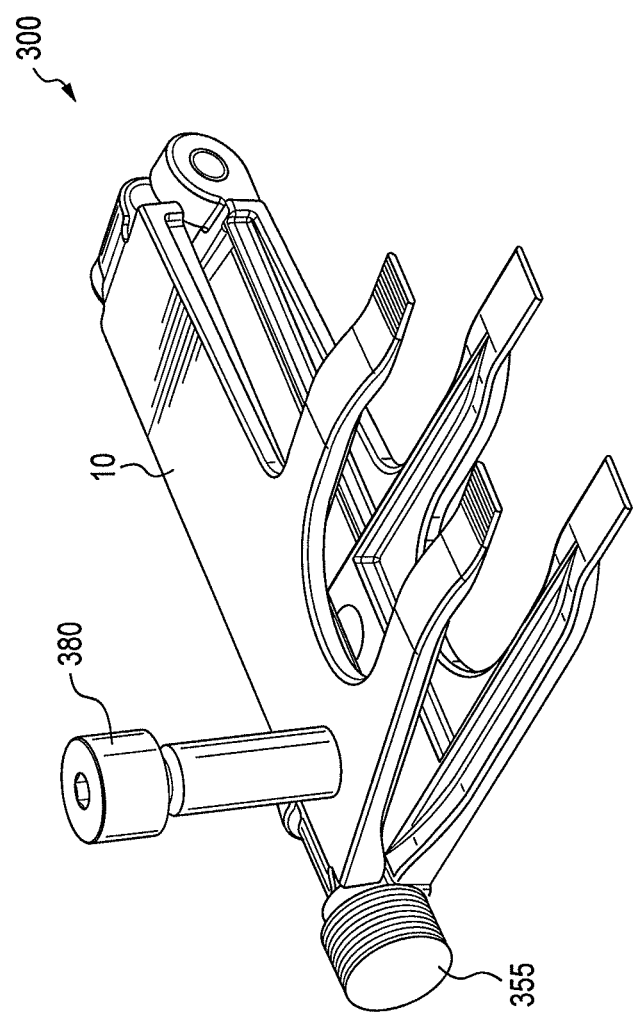

For example, FIGS. 14 and 15 illustrate another exemplary opening jack assembly 200 of the present invention with an adjustable hinge 250 that achieves various AP slope angles. Turning/locking knob 255 is designed to translate along at least a portion of arm 110 (which may optionally be an integral part/structure of upper arm 10) from a first position (shown in FIG. 14) to a second position (shown in FIG. 15).

FIGS. 16-19 illustrate yet another embodiment of an opening jack assembly of the present invention. Opening jack 300 is provided with turning/locking knob 355 which may be configured to engage arms 10, 20 at two different locations relative to the post 380 (i.e., a first location shown in FIGS. 16 and 17, and a second location shown in FIGS. 18 and 19). The assembly provides either a sloped or non-sloped opening, depending upon the surgeon's preference and the plate to be used with the osteotomy.

Description of Use (Opening Jack Assembly 100)

Vertical Opening Configuration i. Position interfacing surfaces of upper and lower bodies coincident and parallel.
ii. Rotate locking knob clockwise until snug.
iii. Rotate one gear on either side of the opening jack to separate the compression arms to the desired displacement.
iv. Insert the adjustment bolt in the threaded hole of either side of the opening jack.

v. Use appropriate size hex head to separate the upper and lower bodies to the desired separation.

AP Opening Configuration vi. Position interfacing surfaces of upper and lower bodies coincident and parallel.

vii. Rotate locking knob counterclockwise until sufficient clearance is made between locking knob and upper and lower bodies, or until snug.

viii. Rotate one gear on either side of the opening jack to separate the compression arms to the desired displacement.

ix. Position the opening jack at the desired opening configuration (right or left AP slope).

x. Insert the adjustment bolt in the threaded hole of either side of opening jack.

xi. Use appropriate size hex head to separate the upper and lower bodies to the desired separation.

Reference is now made to FIG. 20 which illustrates an exemplary opening jack of the present invention, such as opening jack 100, employed in an exemplary open wedge osteotomy procedure in bone (for example, tibia).

An exemplary method for performing an opening wedge osteotomy in a bone comprises inter alia the steps of: (i) forming a cut 91 in bone 90; (ii) providing a mechanical jack 100 comprising a pair of adjustable bodies or plates 10, 20, the pair of plates having a first end and a second end in opposition to one another, the first end of the pair of plates being configured to remain substantially together with one another, and the second end of the pair of plates being configured for placement into the bone cut and for selective positioning from (a) a first position with the second end of the pair of plates substantially together with one another to (b) a second position with the second end of the pair of plates apart from one another and in symmetry with one another, and/or to (c) a third position with the second end of the pair of plates apart from one another and in non-symmetry with one another; (iii) positioning the second ends of the pair of plates of the mechanical jack into the tibia cut 91, the pair of plates having their second ends in the first position with the second ends of the pair of plates substantially together; and (iv) actuating the mechanical jack 100 to move the second ends of the pair of plates from the first position to the second position or the third position with the second ends of the pair of plates apart from each other and either in symmetry or non-symmetry, to distract the bone at the bone cut.

An exemplary method for performing an opening wedge, high tibial osteotomy comprises inter alia the steps of: (i) forming an osteotomy cut 91 in tibia 90; (ii) providing a mechanical jack 100 comprising a pair of adjustable bodies or plates 10, 20 and a locking hinge mechanism 50 attached to the pair of adjustable bodies or plates 10, 20, the locking hinge mechanism 50 comprising a locking knob 55, a horizontal hinge shaft 52, a shaft link 52 and an angle hinge shaft 53, each of the first and second plates being formed of a right arm 10a, 20a, and a left arm 10b, 20b, the pair of plates having a first end and a second end in opposition to one another, the first end of the pair of plates being configured to remain substantially together with one another, and the second end of the pair of plates being configured for placement into the bone cut in the tibia and for selective positioning from (a) a first position wherein the second end of the pair of plates are substantially together with one another to (b) a second position wherein the second end of the pair of plates are apart from one another and with the distance between the right arm 10a of the first plate 10 and the right arm 20a of the second plate 20 being about equal to the distance between the left arm 10b of the first plate 10 and the left arm 20b of the second plate 20, and/or to (c) a third position wherein the second end of the pair of plates are apart from one another and with the distance between the right arm 10a of the first plate 10 and the right arm 20a of the second plate 20 being different from the distance between the left arm 10b of the first plate 10 and the left arm 20b of the second plate 20; (iii) positioning the second ends of the pair of plates of the mechanical jack into the tibia cut, the pair of plates having their second ends in the first position wherein the second ends of the pair of plates are substantially together; (iv) actuating the mechanical jack 50 to move the second ends of the pair of plates from the first position to the second position or the third position wherein the second ends of the pair of plates are apart from each other, to distract the tibia at the osteotomy cut and to form a wedge-like opening 92; and (v) providing an osteotomy plate and securing the osteotomy plate against the tibia and at the wedge-like opening to obtain final repair 99.

While the present embodiments are described herein with reference to illustrative figures for particular applications, it should be understood that the embodiments are not limited thereto. Those having ordinary skill in the art and access to the teachings provided herein, will recognize additional modifications, applications, embodiments and substitution of equivalents all falling within the scope of the presented embodiments.

What is claimed is:

1. An opening jack, comprising:
   a first plate;
   a second plate; and
   a hinge lock mechanism connecting the first plate and the second plate, the hinge lock mechanism configurable in a first position to allow the first plate and the second plate to be adjusted in a vertical direction and configurable in a second position to allow the first plate and the second plate to be adjusted in an anterior-posterior direction;
   wherein the hinge lock mechanism includes a locking knob, a hinge shaft, a shaft link, and an angle hinge shaft.

2. The opening jack as recited in claim 1, wherein the hinge shaft is attached to the locking knob at one end and to the shaft link at the other end.

3. The opening jack as recited in claim 1, wherein the locking knob and the hinge shaft are threaded.

4. The opening jack as recited in claim 1, wherein, when the locking knob is rotated clockwise and tightened, the first plate and the second plate allow only a vertical opening.

5. The opening jack as recited in claim 1, wherein, when the locking knob is rotated counter-clockwise and loosened, the first plate and the second plate allow only an anterior-posterior sloped opening.

6. An opening jack, comprising:
   a first plate;
   a second plate;
   a hinge lock mechanism actuable to lock a positioning of the first plate relative to the second plate in either a vertical direction or an anterior-posterior direction; and
   an adjustment gear mechanism configured to selectively increase or decrease separation of the first plate and the second plate in either the vertical direction or the anterior-posterior direction based on a position of the hinge lock mechanism
   wherein the adjustment gear mechanism includes a first gear and a first adjustable bolt associated with the first plate and a second gear and a second adjustable bolt associated with the second plate.

7. The opening jack as recited in claim 6, wherein each of the first plate and the second plate includes a right arm and a left arm.

8. The opening jack as recited in claim 6, wherein the adjustment gear mechanism includes a first guide post connecting between a first right arm and a first left arm of the first plate and a second guide post connecting between a second right arm and a second left arm of the second plate.

9. The opening jack as recited in claim 6, comprising an impact plate integrally formed as part of one of the first plate and the second plate.

10. The opening jack as recited in claim 9, wherein a hinge shaft of the hinge lock mechanism extends through the impact plate.

11. The opening jack as recited in claim 6, wherein:
in a first position, a first right arm of the first plate is coincident and parallel with a second right arm of the second plate and a first left arm of the first plate is coincident and parallel with a second left arm of the second plate;
in a second position, a first distance between the first right arm of the first plate and the second right arm of the second plate is about similar to a second distance between the first left arm of the first plate and the second left arm of the second plate; and
in a third position, the first distance is different from the second distance.

12. An opening jack, comprising:
a first plate;
a second plate;
a hinge lock mechanism actuable to lock a positioning of the first plate relative to the second plate in either a vertical direction or an anterior-posterior direction; and
an adjustment gear mechanism configured to selectively increase or decrease separation of the first plate and the second plate in either the vertical direction or the anterior-posterior direction based on a position of the hinge lock mechanism;
wherein the hinge lock mechanism includes a locking knob actuable in a first direction to permit vertical displacement of the first plate and the second plate and actuable in a second direction to permit anterior-posterior displacement of the first plate and the second plate.

13. The opening jack as recited in claim 12, wherein the hinge lock mechanism includes a hinge shaft attached to the locking knob at a first end and attached to a shaft link at a second end.

14. The opening jack as recited in claim 13, wherein the hinge lock mechanism includes an angle hinge shaft connected to the shaft link.

\* \* \* \* \*